(12) United States Patent
Kolter et al.

(10) Patent No.: US 7,413,750 B2
(45) Date of Patent: *Aug. 19, 2008

(54) PROCESS FOR PRODUCING SOLID ORAL DOSAGE FORMS WITH SUSTAINED RELEASE OF ACTIVE INGREDIENT

(75) Inventors: Karl Kolter, Limburgerhof (DE); Dieter Flick, Böhl-Iggelheim (DE); Hermann Ascherl, Dirmstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/873,431

(22) Filed: Jun. 5, 2001

(65) Prior Publication Data

US 2002/0012701 A1    Jan. 31, 2002

(30) Foreign Application Priority Data

Jun. 19, 2000   (DE) ............................ 100 29 201

(51) Int. Cl.
*A61K 9/26*   (2006.01)
*A61K 9/14*   (2006.01)
*A61K 9/16*   (2006.01)

(52) U.S. Cl. .............. 424/469; 424/470; 424/486; 424/489; 424/494; 424/497

(58) Field of Classification Search ........ 424/400, 424/464, 468, 469, 470, 484, 486, 489, 494, 424/497; 514/772.4

See application file for complete search history.

(56) References Cited

U.S. PATENT DOCUMENTS

| | | | | |
|---|---|---|---|---|
| 4,801,460 A | * | 1/1989 | Goertz et al. | ............ 514/772.5 |
| 4,837,032 A | * | 6/1989 | Ortega | ........................ 424/469 |
| 5,169,645 A | | 12/1992 | Shuka | |
| 5,389,380 A | * | 2/1995 | Noda et al. | ................. 424/490 |
| 5,403,593 A | | 4/1995 | Royce | |
| 5,453,283 A | | 9/1995 | Muench | |
| 5,874,107 A | | 2/1999 | Fischer | |
| 6,103,264 A | | 8/2000 | Hoffmann | |
| 6,635,279 B2 | * | 10/2003 | Kolter et al. | ................ 424/468 |

FOREIGN PATENT DOCUMENTS

| | | |
|---|---|---|
| DE | 23 57 503 | 5/1975 |
| DE | 38 29398 | 3/1990 |
| DE | 40 31881 | 4/1992 |
| DE | 44 08326 | 9/1995 |
| DE | 197 29487 | 1/1999 |
| EP | 097 523 | 1/1984 |
| EP | 204 596 | 12/1986 |
| GB | 1 442 851 | 7/1976 |

* cited by examiner

*Primary Examiner*—Michael G. Hartley
*Assistant Examiner*—Blessing M Fubara
(74) *Attorney, Agent, or Firm*—Novak Druce + Quigg LLP

(57) ABSTRACT

The present invention relates to a process for producing solid oral dosage forms with sustained release of active ingredient, comprising at least one active ingredient, a preformulated mixture of polyvinyl acetate and polyvinylpyrrolidone, where appropriate, water-soluble polymers or lipophilic additives and, where appropriate, other conventional excipients, wherein this mixture or parts of this mixture are granulated by heating to from 40° C. to 130° C., and the granules are, after admixture with conventional excipients, subsequently tabletted.

17 Claims, No Drawings

PROCESS FOR PRODUCING SOLID ORAL DOSAGE FORMS WITH SUSTAINED RELEASE OF ACTIVE INGREDIENT

The present invention relates to a process for producing solid oral dosage forms with sustained release of active ingredient, comprising at least one active ingredient, a preformulated mixture of polyvinyl acetate and polyvinylpyrrolidone, where appropriate water-soluble polymers or lipophilic additives and, where appropriate, other conventional excipients, wherein this mixture or parts of this mixture are granulated by heating to from 40° C. to 130° C., and the granules are, after admixture with conventional excipients, subsequently tabletted.

So-called depot or sustained release dosage forms are becoming increasingly important especially in pharmaceutical technology. Because it is possible, through the choice of suitable excipients, to control the release of active ingredient, the intention is to improve the therapeutic effect of the dosage form. The release principles in this connection extend from delayed dissolution of active ingredient, the setting up of diffusion barriers or the swelling-based release to chemically controlled release of bioerosion. In practice, the principle of matrix tablets is frequently used.

The production of these sustained release dosage forms, matrix tablets, frequently takes place by granulation and subsequent tabletting. A particular form of agglomeration is represented by melt granulation. In contrast to conventional wet granulation, in which a mixture is moistened with solvent or a binder solution, there is not addition in this process of additional solvent. On the contrary, in this type of agglomeration there is use of binders which are solid at room temperature and melt at temperatures above about 50° C. The omission of additional solvent is particularly interesting since, because there are no drying periods, the process times are distinctly shorter and, in the specific case of water-sensitive active ingredients, it is unnecessary to use organic solvents.

The matrix formers frequently employed are substances from the group of cellulose derivatives, but also substances from the group of fats and waxes. However, since these substances, as well as the active ingredients, can frequently be processed in tablet presses only with difficulty or not at all, because of their physical properties, granulation is often unavoidable.

Many of the matrix formers employed additionally lack a sufficient ability to act also as binders, allowing tablets with adequate mechanical stability to be produced. This therefore frequently makes it necessary to use other excipients which lead not only to stable granules but also to tablets with optimal properties.

In DE 19729487 or DE2357503 there is use of binders which are already molten or are converted into the molten state of aggregation during the process (for example cetyl alcohol, stearyl alcohol or polyethylene glycol). Besides the disadvantage of the change in the state of aggregation, this has the additional disadvantage that the tablet properties are not satisfactory either.

DE 4408326 describes the production of a sustained release tablet with a content of diclofenac-Na. The matrix is formed by using the frequently employed methylhydroxypropylcellulose, which is a associated with the crucial disadvantage that the production of the granules by wet granulation takes place in a fluidized bed, and thus a drying step is made necessary. It is particularly complicated in this case to adjust the release of active ingredient, because this takes place via a two-layer tablet.

DE 3829398 describes a fixed pharmaceutical combination in which, although it is possible to dispense with the use of fillers, there is also a use as matrix formers of stearyl alcohol alone and/or acrylic resins, which must be processed in a melt.

EP 097 523 describes the production of sustained release drugs where the active ingredients represent a combination of salt and the free base. This elaborate process requires several process steps in order to obtain the finished granules. Thus, the actual granules are produced by conventional wet granulation and dried and only then coated with a molten hydrophobic component, or a mixture of such constituents, these usually being fatty alcohols.

U.S. Pat. No. 5,403,593 describes the production of a sustained release dosage form in which a combination of hydrophilic cellulose polymers and a granulating medium with a melting point above 30° C. are employed. It is clear in this case too that a large number of excipients is necessary in order on the one hand to achieve the desired granulation effect, and on the other hand to adjust the release of active ingredient. Although this process can be carried out in one apparatus, in this case cooling of granules to room temperature is necessary before further processing.

Although DE 4 031 881 describes the production of granules which contain, inter alia, polyvinyl acetate as thermoplastic, on the one hand the granules are produced from a melt, and on the other hand the molten active ingredient acts in this process as solvent for the excipient(s) bringing about the sustained release.

U.S. Pat. No. 5,169,645 describes inter alia the production of granules with waxes whose properties can be influenced by the addition of other substances such as, for example, polyvinyl acetate. In this case it is necessary on the one hand for the wax to be molten, and on the other hand for the properties such as, for example, that of release to be adjusted by adding other substances. The situation is similar in the U.S. Pat. No. 5,000,965, where the polyvinyl acetate is melted and additionally mixed with emulsion excipients.

DE 19729487 describes a process for producing active ingredient preparations with controlled release from a matrix. In this case, the release characteristics are adjusted by means of a thermal after-treatment in a fluidized bed. This form of production is very inconvenient because a second step is necessary after the granulation, including changing the operating equipment, in which the granules must be heated again until the melting point of the binder is reached.

EP 0204596 describes the production of microparticles by extrusion. In this process it is necessary to add nonhydrophilic polymers and a mixture of at least two lipid binders, which again makes the overall process very complicated.

DE 3612212 describes the production of pharmaceutical forms by extrusion or injection molding, in which the fusible N-vinylpyrrolidone polymer is employed and, where appropriate, additional nitrogen- and/or oxygen-containing comonomers are included in the polymer. However, in this case, the process requires complete melting of the mixture.

The preparations and processes described above frequently involve the use of very lipophilic, completely melting excipients. In the liquid state of aggregation, these very lipophilic excipients, such as, for example, waxes, dissolve active ingredients and/or completely entrap them. During release therefore the lipophilic drugs which have high affinity for these very lipophilic excipients are not completely released.

The general disadvantage is always that very lipophilic regions exist which are not rendered hydrophilic by hydrophilic polymers. It is therefore impossible for water to penetrate into such regions.

An additional factor is that the compressibility of these lipophilic excipients is very poor. The hardnesses achieved are only low, the friability is high, and adhesion occurs during production, which can be eliminated—if at all—only with very large amounts of release agents.

If the melt granulation aids are added to the powder mixture in the molten state, a problem which often arises is that of uniform distribution of the melt in the powder. An irregular particle structure, poor filling of the die and non-uniform release are the consequence.

Although a number of possibilities for producing sustained release drug forms are now known, there is still a need for simple, rapid and thus cost-effective processes which allow both water-soluble and water-insoluble active ingredients to be used without complications.

It is an object of the present invention to produce active ingredient-containing granules with good physical properties, which can be converted by tabletting into high-dose pharmaceutical dosage forms with sustained release of active ingredient and good mechanical properties. It was intended secondly that the process have short processing times allowing the granules to be produced with relatively little technical complexity and being suitable both for water-sensitive and for water-insensitive active ingredients, with which it is also possible to dispense very substantially with additional excipients.

We have found that this object is achieved by a process for producing an oral dosage form with sustained release of active ingredient, comprising
a) a formulated mixture of polyvinyl acetate and polyvinylpyrrolidone
b) at least one active ingredient
c) where appropriate water-soluble polymers or low or high molecular weight lipophilic additives
d) and, where appropriate, other conventional excipients, wherein the mixture of a) to d) or a) to c) or a) and b) and d) or a) and b) is granulated by heating to from 40° C. to 130° C., and the granules are then tabletted after admixture of conventional excipients.

The process of the invention applies the principle of melt granulation, and a formulated mixture of polyvinyl acetate and polyvinylpyrrolidone acts both as binder and as matrix former, the matrix which is responsible for the sustained release being formed only after the tabletting. The special feature of this process is that no melt is present in the granulation; on the contrary, merely because of the low glass transition temperature ($T_g$) of polyvinyl acetate the surface of the polyvinyl acetate starts to become tacky at temperatures above about 35° C., and thus a granulation effect occurs. The process is in principle independent of the physicochemical properties of the active ingredient. The latter may be water-soluble, water-insoluble, acidic or basic or low-melting.

The invention also relates to the oral dosage forms produced by the process of the invention.

The dosage forms are preferably employed for active pharmaceutical ingredients. However, they can also be employed for any other active ingredient for which delayed release is desired.

The active ingredient or a combination of different active ingredients is premixed alone or with water-soluble or low or high molecular weight lipophilic additives and/or with conventional excipients and the formulated mixture of polyvinyl acetate and polyvinylpyrrolidone, preferably in a mixer, granulated in the same apparatus, continuously or batchwise, by heating to temperatures between 40 and 130° C., preferably in a range from 45 to 100° C. It is possible according to the invention for the granules also to be produced by extrusion or in a fluidized bed. A possible option is to force the granules while still warm or after cooling through a screen with mesh widths between 0.2 mm and 3.0 mm, and then compress them to tablets by adding conventional tabletting excipients such as, for example, fillers or lubricants. The properties of the granules can be adjusted by the skilled worker inter alia via the parameters of temperature and residence time. Higher temperatures and longer residence times usually mean a greater granulation effect and thus coarser particles.

The surface moisture can be increased by adding small amounts of water or solvent (<5%) to the dosage form.

It is surprisingly possible in the process of the invention to employ as mixer both the double cone, ploughshare or V mixers mainly employed for blending, and the sigma kneaders, planetary mixing kneaders, intensive mixers or extruders normally employed in pharmaceutical technology for granulation. It is possible for the energy required for the superficial melting in the mixers to be supplied optionally by means of the heat of friction or conventional heating methods such as, for example, jacket heating or microwaves. A particular advantage which has unexpectedly emerged in this connection is that an apparatus for cooling is not absolutely necessary as in processes employed to date, because this process does not involve a melt in the conventional sense. Adhesion effects and accretions on mixer implements or mixer walls therefore do not occur.

It is possible by adding highly swelling water-soluble polymers or lipophilic additives to vary the release within almost any limits while, at the same time, the flowability of the tabletting mixture is good, and the tablets have great hardness and low friability. It is possible to increase the rate of active ingredient release by adding low-viscosity, nonswelling water-soluble polymers such as polyvinyl alcohols, polyethylene glycols, polyoxyethylene/polyoxypropylene block copolymers, polyvinylpyrrolidones and derivatives, vinyl acetate/vinylpyrrolidone copolymers, preferably polyethylene glycols, polyvinylpyrrolidones, vinyl acetate/vinylpyrrolidone copolymers or maltodextrins.

These additives are employed in concentrations of from 1 to 40%, preferably from 2 to 30%, based on the total weight of the tablets. This is necessary with very low-dose active ingredients, where the amount of formulated mixture of polyvinyl acetate and polyvinylpyrrolidone required to build up the structure entails the release being slowed too much. This also applies to active ingredients of low solubility, where although small amounts of release-slowing agent lead to delayed release, the structure is not completely built up and is subject to wide variations, and the mechanical stability of the tablets is inadequate. This is especially the case when the compressibility of the active ingredient is poor.

The poor flowability of the active ingredient then cannot be decisively improved by small amounts of formulated mixture of polyvinyl acetate and polyvinylpyrrolidone. Increasing the content of release-slowing agent improves these properties, but then leads to release being too slow. The water-soluble nonswelling polymer increases the rate of release and stabilizes the latter to all external effects. The reproducibility is also very much better. Conventional tabletting excipients such as lactose, calcium phosphates, sorbitol, mannitol, microcrystalline cellulose or starch are able to do this insufficiently or not at all. It is probable that an interaction of the water-soluble polymer with a formulated mixture of the polymers polyvinyl acetate and polyvinylpyrrolidone leads to the very stable and reproducible release which is independent of the compressive force. The hardness of the tablets and the friability also show excellent values, and are often in fact better than without admixture of water-soluble polymers.

Water-soluble but swelling, high-viscosity polymers surprisingly lead to slower release. It would have been expected that the inert structure would be destroyed by the swelling polymer, and the active ingredient would be released more rapidly. The fact that this does not occur probably derives from the great elasticity of the formulated mixture of polyvinyl acetate and polyvinylpyrrolidone. The highly viscous solution formed from the water-soluble, swelling polymer in the pores of the structure blocks them and thus slows down diffusion of the active ingredient to the outside. The release is frequently slowed down more than by the two components on their own. A synergistic effect is present. An additional factor is that the initial release is also reduced by gel formation on the surface, and the release profile is thus "linearized". The mechanical properties of the tablets remain at a very high level.

Water-soluble swelling polymers which can be employed are: alginates, pectins, galactomannans, carrageenans, dextran, curdlan, pullulan, gellan, chitin, gelatin, xanthans, hemicelluloses, cellulose derivatives such as methylcellulose, hydroxypropylmethylcellulose, hydroxypropylcellulose, hydroxyethylcellulose, carboxymethylcellulose, starch derivatives such as carboxymethylstarch, degraded starch, maltodextrins, polyacrylic acid, polymethacrylic acid, acrylic acid/methacrylic acid copolymers, polyvinyl alcohols, high molecular weight polyethylene glycols, polyoxyethylene/polyoxypropylene block copolymers, high molecular weight polyvinylpyrrolidones and derivatives thereof.

The ratio of active ingredient to release-slowing agent is between 5:95 and 85:15.

The release-slowing effect can also be intensified by fine-particle lipophilic additives. This entails these additives being trapped in the pores and channels of the structure of polyvinyl acetate and polyvinylpyrrolidone and blocking them. It is important that these substances are employed in small particle size, because they have only a slight effect or no effect in coarse form. Lipophilic additives which can be used are both polymers and low molecular weight compounds. The polymers are, however, preferred.

These additives include: cellulose derivatives such as ethylcellulose, cellulose acetate, cellulose acetate phthalate, cellulose acetate succinate, hydroxypropylmethylcellulose acetate phthalate, hydroxypropylmethylcellulose acetate succinate, acrylic ester/methacrylic ester copolymers, especially methyl methacrylate/ethyl acrylate copolymers, ammoniomethacrylate copolymer type A and type B, methacrylic acid/acrylic ester copolymers, especially methacrylic acid/ethyl acrylate copolymers, fatty alcohols such as stearyl alcohol, fatty acids such as stearic acid, fatty acid esters and fatty alcohol esters, glycerides, waxes, lecithin.

Water-soluble additives which can be employed are the following:

Polyvinyl alcohols, polyethylene glycols, polyoxyethylene/polyoxypropylene block copolymers, polyvinylpyrrolidone and derivatives, vinyl acetate/vinylpyrrolidone copolymers, preferably polyethylene glycols, polyvinylpyrrolidones, vinyl acetate/vinylpyrrolidone copolymers or maltodextrins, and salts thereof.

These additives are employed in concentrations of from 1 to 40%, preferably from 2 to 30%, based on the total weight of the tablets.

The formulated mixture of polyvinyl acetate and polyvinylpyrrolidone is present in the preparations of the invention in concentrations of from 10 to 80%, preferably from 20 to 60%. The molecular weights of polyvinyl acetate and polyvinylpyrrolidone are in each case between 20 000 and 1 000 000.

The ratio of polyvinyl acetate and polyvinylpyrrolidone in the formulated mixture is between 6:4 and 9:1, preferably 8:2. This formulation is designed so that the polyvinylpyrrolidone is extremely finely dispersed in the polyvinyl acetate.

The dosage forms of the invention comprise oral dosage forms such as tablets, extrudates, pellets or granules.

Smaller shaped articles such as, for example, pellets or microtablets can also be introduced into capsules.

Dosage forms of this invention are distinguished by the fact that additional excipients are not absolutely necessary and accordingly solid drug forms with a high active ingredient content can be produced. If, nevertheless, excipients are used in order to adjust particular properties, they are substances from the class of fillers such as, for example, lactose, cellulose powder, mannitol, calcium diphosphate or various starches, silicates, and disintegrants and adsorbents, lubricants, flowability agents, dyes, stabilizers such as antioxidants, wetting agents, preservatives, release agents, flavorings or sweeteners, preferably fillers.

Lubricants which can be used are stearates of aluminum, calcium, magnesium and tin, and magnesium silicate, silicones and the like.

Flowability agents can be, for example, talc or colloidal silica.

An example of a binder is microcrystalline cellulose.

Disintegrants can be crosslinked polyvinylpyrrolidone or crosslinked sodium carboxymethylstarch. Stabilizers can be ascorbic acid or tocopherol.

Examples of fillers which can be added are inorganic fillers such as oxides of magnesium, aluminum, silicon, titanium carbonate or calcium carbonate, calcium phosphates or magnesium phosphates or organic fillers such as lactose, sucrose, sorbitol, mannitol.

Examples of dyes are iron oxides, titanium dioxide, triphenylmethane dyes, azo dyes, quinoline dyes, indigotine dyes, carotenoids, for coloring the dosage forms, opacifying agents such as titanium dioxide or talc in order to reduce the transparency to light and to save on dyes.

The dosage forms of the invention may contain any active ingredient for which delayed release is desired.

The active ingredients preferably employed are food supplements or additives, vitamins, minerals or trace elements, but particularly preferably active pharmaceutical ingredients.

Pharmaceutical formulations of the abovementioned type can be obtained by processing the claimed compounds with active pharmaceutical ingredients by conventional methods and with use of known and novel active ingredients. The active ingredients may moreover come from any area of indications.

Examples which may be mentioned here are the following:

Benzodiazepines, antihypertensives, vitamins, cytostatics, anesthetics, neuroleptics, antidepressants, antibiotics, antimycotics, fungicides, chemotherapeutics, urologicals, platelet aggregation inhibitors, sulfonamides, spasmolytics, hormones, immunoglobulins, sera, thyroid therapeutics, psychopharmaceuticals, antiparkinson agents and other antihyperkinetics, ophthalmologicals, neuropathy products, calcium metabolism regulators, muscle relaxants, lipid-lowering agents, liver therapeutics, coronary agents, cardiac agents, immunotherapeutics, regulatory peptides and their inhibitors, hypnotics, sedatives, gynecologicals, antigout agents, fibrinolytics, enzyme products and transport proteins, enzyme inhibitors, emetics, perfusion promoters, diuretics, diagnostics, corticoids, cholinergics, biliary therapeutics, antiasthmatics, bronchospasmolytics, beta-receptor blockers, calcium channel blockers, ACE inhibitors, arteriosclesis remedies, antiinflammatory agents, anticoagulants, antihypotensives, antihypoglycemics, antifibrinolytics, antiepileptics, antiemetics, antidotes, antidiabetics, antiarrhythmics, antianemics, antiallergics, anthelmintics, analgesics, analeptics, aldosterone antagonists, weight-reducing agents.

Surprisingly, any active ingredient which does not decompose at the stated temperatures and whose average particle size is in a range between 20 and 700 μm, but preferably in a range between 30 and 500 μm is suitable.

The shape of the tablet can be varied within wide limits. Thus, biconvex, biplanar, round or polygonal tablets can be produced, as well as oblong or football shapes. The upper limit on size is determined by the swallowability, while the lower limit is determined by machine design limits. Conventional tablet sizes are between 1 and 16 mm, preferably between 2 and 13 mm, in diameter.

It is also possible to produce two-layer or multilayer tables in which one layer contains the complete dose of active ingredient or at least has a very large active ingredient content, whereas the other layer has a very large content of the polyvinyl acetate/polyvinylpyrrolidone combination. It is possible in this way specifically to influence active ingredient release additionally. It is even possible on use of two or more active ingredients to release these at different rates by incorporating them entirely or for the most part separately in individual layers.

Besides the formulated mixture of polyvinyl acetate and polyvinylpyrrolidone, it is additionally possible to add release-sustaining excipients. The addition can optionally take place both before and after the granulation.

The combination of the two polymers polyvinyl acetate and polyvinylpyrrolidone makes it possible by means of the chosen process to produce granules in a "one-pot system", it being possible to dispense with the addition of any solvents, and it being unnecessary either for an additional thermal after-treatment to be carried out or for the tablets to be coated. Another advantage is that active ingredients whose tablettability is known to be poor can be processed in a simple manner.

The particular advantages of the produced granules are immediately evident in the properties of the granules of paracetamol (fine crystals type) which is known to be difficult to process. On the basis of the distinctly better flow characteristics, the first advantage of the granules produced by melt granulation from polyvinyl acetate and polyvinylpyrrolidone in the ratio 8:2 (Kollidon SR) is evident compared with other matrix formers frequently used.

TABLE 1

Flow properties of paracetamol granules

| Granule composition | Angle of repose | Flow time |
|---|---|---|
| Paracetamol/Kollidon SR (1:1)[1] | 32.9° | 7.84 s |
| Paracetamol/Methocel K 15M (1:1)[1] | 48.2° | flow stops |
| Paracetamol/stearyl alcohol (1:1)[2] | 45.6° | flow stops |
| Paracetamol/Kollidon SR (1:1)[3] | 34.2° | flow stops |

[1]Granulation in a type UMC5 electronic Stephan mixer (from A. Stephan u. Söhne)
Parameters: 85° C. (jacket heating), 12.5 min, 650 rpm
[2]Granulation in an intensive mixer (Diosna V20)
Parameter: 12.5 min
[3]Physical mixture The angle of repose was determined by the Pfrengle method specified in DIN 53916.

The dosage forms of the invention show good hardnesses and uniformities of weight for the tablets produced from the granules. The paracetamol/Methocel K 15M combination granule properties are distinctly worse, resulting in the relative standard deviation for the tablet masses being twice as large, and the poor hardnesses. In order to improve the tablet properties it was therefore frequently necessary for additional binders and satisfactorily compressible fillers to be added.

TABLE 2

Properties of paracetamol tablets

| Tablet composition | Hardness | Weight | srel |
|---|---|---|---|
| Paracetamol/Kollidon SR (1:1)[1] | 175 N | 319.0 mg | 0.4% |
| Paracetamol/Methocel K 15M (1:1)[1,2] | 112 N | 320.5 mg | 0.8% |
| Paracetamol/stearyl alcohol (1:1)[1,2] | 53 N | 311.8 mg | 0.6% |

[1]Tabletting in a Korsch (type Ek0) eccentric press
Excipient: 0.5% magnesium stearate
Punch: 10 mm, beveled; compressive force: 18 kN
[2]Additional excipient: 1.0% Aerosil 200

The tablet properties (hardness and tablet weight) were measured using an automatic tablet tester from Kraemer (type HT-TMB).

On use of a formulated mixture of polyvinyl acetate and polyvinylpyrrolidone the tablet properties achieved without the addition of other fillers are excellent, even with products whose tablettability is poor.

In contrast to conventional methods, it is possible with the method of the invention by simple manipulation to produce sustained release tablets which are distinguished by good mechanical properties and easily adjustable release characteristics.

EXAMPLE 1

400 g of a Kollidon SR/paracetamol mixture composed of 50% Kollidon SR and 50% paracetamol were premixed in a Stephan mixer with jacket heating and granulated at various temperatures (70 to 85° C.) and at 650 rpm for various times. The still hot granules were then passed through a 1 mm screen, leading to very homogeneous granules. After admixture of 0.5% magnesium stearate, 10 mm beveled tablets were produced in a Korsch Ek0 eccentric press.

Table 3 shows the dependence of the granule particle size on the granulation temperature and the residence time, the granulation effects achieved being, as expected, better with a longer granulation time and higher granulation temperature.

TABLE 3

Dependence of the average particle size on the granulation temperature and the granulation time

| Granulation time [min] | Granulation temperature [° C.] | | |
|---|---|---|---|
| | 75 | 80 | 85 |
| 7.5 | 147.4 μm | 146.2 μm | 279.2 μm |
| 12.5 | 157.6 μm | 164.6 μm | 391.8 μm |
| 17.5 | 179.7 μm | 296.8 μm | 416.6 μm |

The average particle size was measured by laser diffraction. The D[4,3] value is stated.

EXAMPLE 2

400 g of a Kollidon SR/paracetamol mixture composed of 50% Kollidon SR and 50% paracetamol were premixed in a Stephan mixer with jacket heating and granulated at about 80° C. and at 650 rpm for 12.5 min. The paracetamol employed had previously been fractionated in order to establish the effect of the active ingredient particle size on the granulation. The still hot granules were passed through a 1 mm screen, leading to very homogeneous granules. After admixture of 0.5% magnesium stearate, 10 mm beveled tablets were produced in a Korsch Ek0 eccentric press.

Table 4 shows that even small active ingredient particles can be granulated without problems, and that there is no dusting, as might be suspected, of the polymer particles, thus preventing granulation.

TABLE 4

Dependence of the average particle size of the granules on the average particle size of the active ingredient

| Average particle size of active ingredient [μm] | Average particle size of granules [μm] |
| --- | --- |
| 58.0 | 182.6 |
| 63.1 | 178.3 |
| 92.8 | 287.9 |
| 116.8 | 502.2 |
| 179.4 | 590.2 |
| 412.2 | 640.1 |
| 557.6 | 655.3 |
| 685.2 | 672.7 |
| 930.9 | 707.1 |

The average particle size was measured by laser diffraction. The D[4,3] value is stated.

Table 5 shows that there are only slight effects on the hardness despite distinct differences in the starting material.

TABLE 5

Dependence of the hardness on the average particle size of the active ingredient

| Average particle size of active ingredient [μm] | Hardness [N] |
| --- | --- |
| 58.0 | 157 |
| 63.1 | 148 |
| 92.8 | 148 |
| 116.8 | 170 |
| 179.4 | 183 |
| 412.2 | 161 |
| 557.6 | 167 |
| 685.2 | 159 |
| 930.9 | 156 |

The hardness was measured using an automatic tablet tester from Kraemer (type HT-TMB).

Table 6 shows the active ingredient release from tablets by the paddle method in deionized water at 37° C. over 16 h.

TABLE 6

Dependence of the active ingredient release on the average particle size

Active ingredient released [%]

| Time [h] | Average particle size of granules = 178 μm (active ingredient = 63 μm) | Average particle size of granules = 590 μm (active ingredient = 179 μm) |
| --- | --- | --- |
| 0.5 | 12.5 | 13.4 |
| 1.0 | 17.8 | 18.8 |
| 1.5 | 21.5 | 23.0 |
| 2.0 | 25.1 | 26.4 |
| 3.0 | 31.2 | 30.0 |
| 4.0 | 35.0 | 33.6 |
| 6.0 | 40.4 | 40.3 |
| 8.0 | 44.2 | 44.7 |
| 12.0 | 50.7 | 52.2 |
| 16.0 | 58.1 | 57.9 |

EXAMPLE 3

400 g of a Kollidon SR/theophylline mixture composed of
a) 50% Kollidon SR and 50% theophylline
b) 43.75% Kollidon SR and 56.25% theophylline
c) 37.5% Kollidon SR and 62.5% theophylline
d) 25% Kollidon SR and 75% theophylline were premixed in a Stephan mixer with jacket heating and granulated at about 85° C. and at 650 rpm for 12.5 min. The still hot granules were then passed through a 1 mm screen, leading to homogeneous granules each time. After admixture of 0.5% magnesium stearate and 1% Aerosil 200, 10 mm beveled tablets were produced in a rotary press (Korsch PH 106). Release took place in analogy to example 2.

Table 7 shows clearly the effect of the amount of Kollidon SR on the active ingredient release and on the hardness.

TABLE 7

Properties of theophylline tablets

| Tablet composition | Hardness | $t_{50}$ |
| --- | --- | --- |
| a[1] | 220 N | >16 h |
| b[1] | 202 N | 15.2 h |
| c[1] | 186 N | 12.3 h |
| d[1] | 153 N | 11.6 h |

[1]Tabletting in a Korsch rotary press (Korsch PH 106)
Excipients: 1.0% Aerosil 200; 0.5% magnesium stearate
Punch: 10 mm, beveled; compressive force: 18 kN The hardness was measured in an automatic tablet tester from Kraemer (type HT-TMB). The release time for determining the $t_{50}$ of the tablets was 16 h (paddle method; test medium: 0 to 2 h: 0.1 N HCl, 2 to 16 h: phosphate buffer pH 6.8; test temperature: 37° C.).

EXAMPLE 4

400 g of a Kollidon SR/caffeine/alginate mixture composed of 47.5% Kollidon SR, 47.5% paracetamol and 5% alginate were premixed in a high-speed mixer with jacket heating (Gral Collette type) and granulated at a temperature of about 85° C. The still hot granules were then passed through a 1 mm screen, leading to homogeneous granules each time. After a granulation time of about 10 min, the granules were passed through a 1 mm screen and, after admixture of 0.5% magnesium stearate, 10 mm beveled tablets were produced in an eccentric press (Korsch Ek0).

The tablets have a hardness of about 160 N even with a compressive force of 10 kN.

EXAMPLE 5

The fact that a release-slowing effect is achieved only after tabletting was demonstrated on the basis of the following experiment (Kollidon SR/paracetamol 1:1) through the release from a) the physical mixture
b) the granules (Stephan mixer: 650 rpm, 85° C., 12.5 min)
c) tablets produced from the physical mixture (10 mm, beveled; compressive force: 18 kN)
d) tablets produced from the granules (10 mm, beveled; compressive force: 18 kN)

Table 8 shows that there is no release-slowing effect either with the physical mixture or with the melt granules. An effect is evident only after tabletting, the release being delayed even more from the tablet produced from the melt granules. This result shows that the process of melt granulation of the invention distinctly enhances the release-slowing effect in the tablet with the formulated mixture of polyvinylacetate and polyvinylpyrrolidone, preferably in the ratio 8:2.

TABLE 8

Dependence of active ingredient release on the dosage form

| | Active ingredient released [%] | | | |
|---|---|---|---|---|
| Time [h] | Physical mixture | Granules (650 rpm, 85° C. 12.5 min) | Tablet from granules[1] | Tablet from physical mixture[1,2] |
| 0.5 | 99.8 | 100.1 | 10.6 | 11.5 |
| 1.0 | | | 15.4 | 18.0 |
| 1.5 | | | 18.4 | 20.9 |
| 2.0 | | | 21.4 | 25.0 |
| 3.0 | | | 24.0 | 29.9 |
| 4.0 | | | 27.5 | 31.8 |
| 6.0 | | | 32.9 | 28.4 |
| 8.0 | | | 33.5 | 44.4 |
| 12.0 | | | 41.6 | 52.7 |
| 16.0 | | | 47.7 | 58.3 |

[1]Tabletting in a Korsch eccentric press (type Ek0)
Excipient: 0.5% magnesium stearate
Punch: 10 mm, beveled; compressive force: 18 kN
[2]Additional excipient: 1.0% Aerosil 200

Active ingredient release from the tablets was carried out by the paddle method in deionized water at 37° C. over 16 h.

EXAMPLE 6

A Kollidon SR/caffeine mixture composed of 50% Kollidon SR and 50% caffeine was mixed in a drum mixer (from Turbula, type T 10B). The mixture was kneaded in a single screw extruder (from Haake, type Rheocord 90) at a temperature of 50° C. to give a homogeneous composition. The strands were cut by a cutting device to give granules which were again passed through a 1 mm screen and, after admixture of 0.5% magnesium stearate, compressed to 10 mm beveled tablets in an eccentric press (Korsch Ek0).

TABLE 9

Comparison of the average particle size of the physical mixture with the granules

| | Caffeine/Kollidon SR (1:1) |
|---|---|
| Average particle size of physical mixture | 80.23 μm |
| Average particle size of granules | 553.88 μm |

The average particle size was measured by laser diffraction. The D[4,3] value is stated.

Comparative Example
Hydroxypropylmethylcellulose 400 g of a Methocel K15M/paracetamol mixture composed of 50% Methocel K15M and 50% paracetamol were premixed in a Stephan mixer with jacket heating and granulated at about 85° C. and at 650 rpm for 12.5 min. The still hot mixture was passed through a 1 mm screen. After admixture of 0.5% magnesium stearate and 1% Aerosil 200, 10 mm beveled tablets were produced in a Korsch Ek0 eccentric press.

In addition to the absence of a granulation effect, the flow properties are distinctly worse and the tablet properties are worse. The brittle paracetamol in fact results in particle comminution, as a result of fracture of crystals, in place of granulation.

TABLE 10

Comparison of granule and tablet properties

| | Paracetamol/Kollidon SR (1:1)[1,2] | Paracetamol/Methocel K 15M (1:1)[1,2,3] |
|---|---|---|
| Particle size D[4,3] [μm] (physic. mixture) | 115.91 | 154.97 |
| Particle size D[4,3] [μm] granules) | 539.17 | 139.34 |
| Angle of repose [°] | 32.90 | 48.20 |
| Flow time [s] | 7.84 | flow stops |
| Hardness [N] | 175.00 | 112.00 |
| Weight [mg] (srel [%]) | 319 (0.4) | 320.5 (0.8) |
| $t_{50}$ [h] | >16 | 12.9 |

[1]Granulation in a Stephan type UMC5 electronic mixer (from A. Stephan u. Söhne)
Parameters: 85° C. (jacket heating), 12.5 min, 650 rpm
[2]Tabletting in a Korsch eccentric press (type Ek0)
Excipient: 0.5% magnesium stearate
Punch: 10 mm, beveled; compressive force: 18 kN
[3]Additional excipient: 1.0% Aerosil 200

The average particle size was measured by laser diffraction. The D[4,3] value is stated. The angle of repose was determined by the Pfrengle method as described in DIN 53916. The tablet properties were determined using an automatic tablet tester from Kraemer (type HT-TMB). The release time for determining the $t_{50}$ of the tablets was 16 h at 37° C. in deionized water (paddle method).

Comparative Example Stearyl Alcohol

The molten stearyl alcohol is added to the paracetamol in an intensive mixer and granulated for 12.5 min. The cooled granules are passed through a 1 mm screen. After admixture of 0.5% magnesium stearate and 1% Aerosil 200, 10 mm beveled tablets were produced in a Korsch Ek0 eccentric press.

In addition to the poor flow characteristics, the tablet properties are distinctly worse. Tabletting with a compressive force of 18 kN was possible under the same conditions as in Example 1 only with provisos because every second tablet was capped on ejection from the die. The intact tablets have low hardness and a friability of 100%.

TABLE 11

Comparison of the granule and tablet properties

| | Paracetamol/Kollidon SR (1:1)[1,3] | Paracetamol/ stearyl alcohol (1:1)[2,3,4] |
|---|---|---|
| Angle of repose [°] | 32.9 | 45.57 |
| Flow time [s] | 7.84 | flow stops |
| Hardness [N] | 175 | 53 |
| Weight [mg] (srel [%]) | 319 (0.4) | 311.8 (0.6) |
| $t_{50}$ [h] | >16 | 4.8 |

[1]Granulation in the Stephan type UMC5 electronic mixer (from A. Stephan u. Söhne)
Parameters: 85° C., 12.5 min, 650 rpm
[2]Granulation in an intensive mixer (Diosna V20), 12.5 min
[3]Tabletting in a Korsch eccentric press (type Ek0)
Excipient: 0.5% magnesium stearate
Punch: 10 mm, beveled; compressive force: 18 kN
[4]Additional excipient: 1.0 Aerosil 200

The angle of repose was determined by the Pfrengle method specified in DIN 53916. The tablet properties were measured using an automatic tablet tester from Kraemer (type HT-TMB). The release time for determining the $t_{50}$ of the tablets was 16 h at 37° C. in deionized water (paddle method).

We claim:

1. A process for producing an oral dosage form with sustained release of active ingredient, wherein the dosage form comprises
   a) a formulated mixture of polyvinyl acetate and polyvinylpyrrolidone which acts as a binder and a matrix former, and wherein the polyvinylpyrrolidone has a molecular weight of from 20,000 to 1,000,000, and the polyvinylpyrrolidone is finely dispersed in the polyvinyl acetate,
   b) at least one active ingredient,
   c) optionally water-soluble polymers or low or high molecular weight lipophilic additives,
   d) and, optionally, excipients, wherein the process comprises granulating a mixture of a) to d) or a) to c) or a) and b) and d) or a) and b) by heating to a temperature of from 40° C. to 130° C. in the absence of solvents.

2. A process as claimed in claim 1, wherein the polyvinyl acetate to polyvinylpyrrolidone ratio is 6:4 to 9:1.

3. A process as claimed in claim 1, wherein the active ingredient water-soluble polymers or low or high molecular weight lipophilic additives ratio employed is from 5:95 to 85:15.

4. A process as claimed in claim 1, wherein polyvinyl acetate and polyvinylpyrrolidone each have a molecular weight of from 20,000 to 1,000,000.

5. A process as claimed in claim 1, wherein the mixture is granulated by heating to from 45 to 100° C.

6. A process as claimed in claim 1, wherein the particle size of the active ingredients employed is in a range from 20 to 700 μm.

7. A process as claimed in claim 1, wherein the excipients employed are fillers, disintegrants and adsorbents, lubricants, flowability agents, dyes, stabilizers, antioxidants, wetting agents, preservatives, release agents, flavorings or sweeteners.

8. A process as claimed in claim 1, wherein fillers selected from the group consisting of lactose, cellulose powder, mannitol, calcium diphosphate and starch are employed as excipients.

9. A process as claimed in claim 1, wherein the granules can be produced by employing the process of mixer granulation, fluidized bed granulation or extrusion granulation.

10. A process as claimed in claim 1, wherein besides the formulated mixture of polyvinyl acetate and polyvinylpyrrolidone, further release-sustaining excipients may optionally be employed before, during or after the granulation.

11. A process as claimed in claim 1, wherein water-soluble, water-soluble highly swelling or lipophilic excipients are employed for further modification of release.

12. A process as claimed in claim 1, wherein the water-soluble polymers are selected from the group consisting of: polyvinyl alcohols, polyethylene glycols, polyoxyethylene/polyoxypropylene block copolymers, polyvinylpyrrolidones, vinyl acetate/vinyl pyrrolidone copolymers, polyethylene glycols, polyvinylpyrrolidones, vinyl acetate/vinylpyrrolidone copolymers, maltodextrins, and salts thereof.

13. A process as claimed in claim 1, wherein the production is either continuously or batchwise.

14. A process as claimed in claim 1, wherein the granulated mixture is further processed by forced screening of the granules in the hot state or in the cooled state.

15. A process as claimed in claim 1, wherein the water-soluble polymers are selected from the group consisting of alginates, pectins, galactomannans, carrageenans, dextran, curdlan, pullulan, gellan, chitin, gelatin, xanthans, hemicelluloses, cellulose derivatives selected from the group consisting of methylcellulose, hydroxypropylmethylcellulose, hydroxypropylcellulose, hydroxyethylcellulose and carboxymethylcellulose, starch derivatives selected from the group consisting of carboxymethylstarch and degraded starch, maltodextrins, polyacrylic acid, polymethacrylic acid, acrylic acid/methacrylic acid copolymers, polyvinyl alcohols, high molecular weight polyethylene glycols, polyoxyethylene/polyoxypropylene block copolymers and high molecular weight polyvinylpyrrolidones.

16. A process as claimed in claim 1, wherein the lipophilic additives are selected from the group consisting of fatty alcohols, fatty acids, glycerides, fatty acid esters, fatty alcohol esters and lipophilic polymers.

17. A process as claimed in claim 16, wherein the fatty alcohol is stearyl alcohol; the fatty acid is stearic acid; and the lipophilic polymers are selected from the group consisting of ethylcellulose, cellulose acetate, acrylic ester/methacrylic ester copolymers, methacrylic acid/acrylic ester copolymers, cellulose acetate phthalate, cellulose acetate succinate, hydroxypropylmethylcellulose acetate phthalate and hydroxypropyl-methylcellulose acetate succinate.

* * * * *